United States Patent
Rounbehler et al.

(10) Patent No.: US 10,814,092 B2
(45) Date of Patent: *Oct. 27, 2020

(54) CONVERSION OF NITROGEN DIOXIDE (NO₂) TO NITRIC OXIDE (NO)

(71) Applicant: VERO BIOTECH LLC, Atlanta, GA (US)

(72) Inventors: David P. Rounbehler, Lexington, MA (US); David H. Fine, Cocoa Beach, FL (US)

(73) Assignee: VERO Biotech LLC, Atlanta, GA (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/186,790

(22) Filed: Nov. 12, 2018

(65) Prior Publication Data

US 2019/0143068 A1    May 16, 2019

Related U.S. Application Data

(63) Continuation of application No. 15/385,354, filed on Dec. 20, 2016, now Pat. No. 10,124,142, which is a continuation of application No. 14/107,629, filed on Dec. 16, 2013, now Pat. No. 9,522,249, which is a continuation of application No. 13/555,567, filed on Jul. 23, 2012, now Pat. No. 8,609,028, which is a continuation of application No. 13/298,970, filed on Nov. 17, 2011, now Pat. No. 8,226,916, which is a continuation of application No. 12/500,929, filed on Jul. 10, 2009, now Pat. No. 8,083,997, which is a continuation of application No. 11/206,305, filed on Aug. 18, 2005, now Pat. No. 7,560,076.

(Continued)

(51) Int. Cl.
| | |
|---|---|
| A61M 16/12 | (2006.01) |
| A61M 16/10 | (2006.01) |
| C01B 21/24 | (2006.01) |
| A61D 7/04 | (2006.01) |
| A61M 16/00 | (2006.01) |
| A61M 15/00 | (2006.01) |

(52) U.S. Cl.
CPC ............... *A61M 16/12* (2013.01); *A61D 7/04* (2013.01); *A61M 16/0057* (2013.01); *A61M 16/10* (2013.01); *A61M 16/104* (2013.01); *C01B 21/24* (2013.01); *A61M 15/00* (2013.01); *A61M 2016/102* (2013.01); *A61M 2202/0275* (2013.01)

(58) Field of Classification Search
USPC .................. 422/120, 122; 95/102, 105, 106; 128/200.24, 203.26
See application file for complete search history.

(56) References Cited

U.S. PATENT DOCUMENTS 3,106,458 A * 10/1963 Grosskopf ............. G01N 31/22
                                                    436/117
3,958,580 A *  5/1976 Mergens ............... A24B 15/245
                                                    131/352

(Continued)

*Primary Examiner* — Nina Bhat

(57) ABSTRACT

Inhalation of low levels of nitric oxide can rapidly and safely decrease pulmonary hypertension in mammals. A nitric oxide delivery system that converts nitrogen dioxide to nitric oxide employs a surface-active material, such as silica gel, coated with an aqueous solution of antioxidant, such as ascorbic acid.

17 Claims, 15 Drawing Sheets

Related U.S. Application Data

(60) Provisional application No. 60/602,333, filed on Aug. 18, 2004.

(56) References Cited

U.S. PATENT DOCUMENTS

| | | | | |
|---|---|---|---|---|
| 4,221,761 A * | 9/1980 | Bullens | B01D 53/56 422/54 |
| 4,287,040 A * | 9/1981 | Alamaro | B01J 19/088 204/179 |
| 4,399,942 A * | 8/1983 | Chand | G01N 33/0006 239/34 |
| 4,774,069 A * | 9/1988 | Handley | C01B 21/267 423/403 |
| 5,514,204 A * | 5/1996 | Sheu | B01D 53/04 95/92 |
| 5,558,083 A * | 9/1996 | Bathe | A61M 16/12 128/203.12 |
| 5,615,669 A * | 4/1997 | Olsson | A61M 16/12 128/203.12 |
| 5,651,358 A * | 7/1997 | Briend | A61M 16/12 128/203.12 |
| 5,692,495 A * | 12/1997 | Sheu | A61K 33/00 128/203.12 |
| 5,839,433 A * | 11/1998 | Higenbottam | A61M 16/204 128/204.21 |
| 5,846,297 A * | 12/1998 | Schleicher | A61K 33/00 95/129 |
| 5,871,009 A * | 2/1999 | Rydgren | A61M 16/12 128/203.12 |
| 5,873,359 A * | 2/1999 | Zapol | A61K 9/0078 128/200.14 |
| 5,994,444 A * | 11/1999 | Trescony | A61L 29/085 524/429 |
| 6,103,275 A * | 8/2000 | Seitz | A61K 9/0014 424/718 |
| 6,109,260 A * | 8/2000 | Bathe | A61M 16/10 128/203.12 |
| 6,190,704 B1 * | 2/2001 | Murrell | A61K 31/145 424/718 |
| 6,576,044 B1 * | 6/2003 | Ho | B01D 53/02 95/102 |
| 6,635,273 B1 * | 10/2003 | Loscalzo | A61K 31/135 424/400 |
| 6,749,834 B2 * | 6/2004 | Fein | A61M 15/08 128/200.11 |
| 6,758,214 B2 * | 7/2004 | Fine | A61K 33/00 128/203.12 |
| 7,040,313 B2 * | 5/2006 | Fine | A61K 33/34 128/203.12 |
| 7,288,664 B2 * | 10/2007 | Kleiner | C07D 307/62 549/315 |
| 7,560,076 B2 * | 7/2009 | Rounbehler | A61M 16/10 422/120 |
| 7,618,594 B2 * | 11/2009 | Rounbehler | A61M 16/10 422/120 |
| 7,914,743 B2 * | 3/2011 | Fine | A61K 33/00 422/120 |
| 7,947,227 B2 * | 5/2011 | Fine | A61M 16/10 422/120 |
| 8,083,997 B2 * | 12/2011 | Rounbehler | A61M 16/10 422/120 |
| 8,607,785 B2 * | 12/2013 | Fine | A61M 16/10 128/202.26 |
| 8,887,720 B2 * | 11/2014 | Fine | A61M 16/12 128/202.26 |
| 2001/0012851 A1 * | 8/2001 | Lundy | A61K 31/404 514/418 |
| 2003/0062043 A1 * | 4/2003 | Fine | A61K 33/34 128/203.12 |
| 2010/0043787 A1 * | 2/2010 | Fine | A61M 16/10 128/202.26 |
| 2011/0262335 A1 * | 10/2011 | Fuller | F16L 37/101 423/239.1 |
| 2013/0309328 A1 * | 11/2013 | Watts | A61K 31/13 424/718 |
| 2014/0373836 A1 * | 12/2014 | Potenziano | A61K 33/00 128/203.12 |
| 2015/0053544 A1 * | 2/2015 | Igney | A61K 33/00 204/157.44 |

* cited by examiner

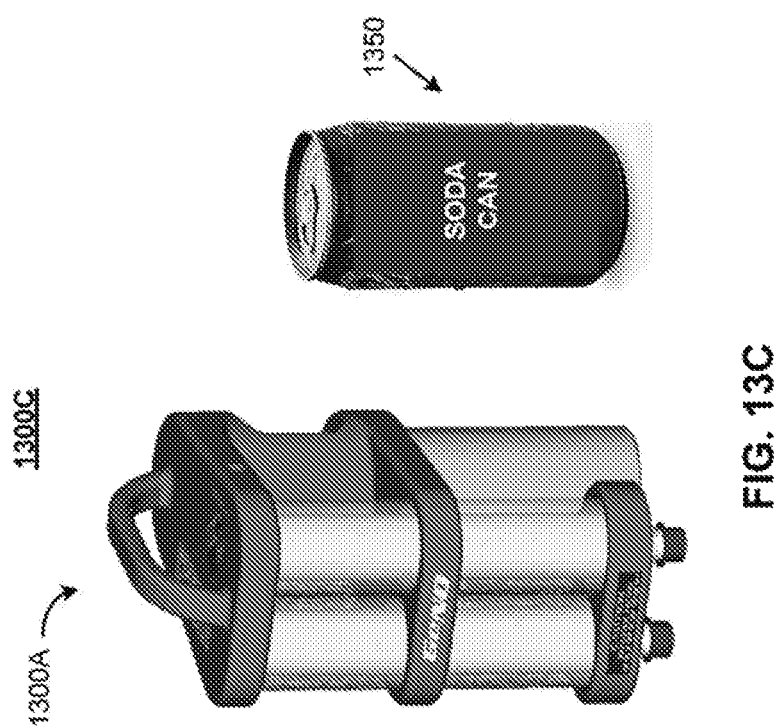

CONVERSION OF NITROGEN DIOXIDE (NO₂) TO NITRIC OXIDE (NO)

CROSS REFERENCE TO RELATED APPLICATIONS

This application is a continuation of U.S. application Ser. No. 15/385,354, filed Dec. 20, 2016, now U.S. Pat. No. 10,124,142, which is a continuation of U.S. application Ser. No. 14/107,629, filed Dec. 16, 2013, now U.S. Pat. No. 9,522,249, which is a continuation of U.S. application Ser. No. 13/555,567, filed Jul. 23, 2012, now U.S. Pat. No. 8,609,028, which is a continuation of U.S. application Ser. No. 13/298,970, filed Nov. 17, 2011, now U.S. Pat. No. 8,226,916, which is a continuation of U.S. application Ser. No. 12/500,929, filed Jul. 10, 2009, now U.S. Pat. No. 8,083,997, which is a continuation of U.S. application Ser. No. 11/206,305, filed Aug. 18, 2005, now U.S. Pat. No. 7,560,076, which claim the benefit of U.S. Provisional Application No. 60/602,333, filed Aug. 18, 2004, and entitled CONVERSION OF NITROGEN DIOXIDE (NO₂) TO NITRIC OXIDE (NO), each of which is incorporated by reference in its entirety.

TECHNICAL FIELD

This description relates to controllably generating nitric oxide.

BACKGROUND

Nitric oxide (NO), also known as nitrosyl radical, is a free radical that is an important signaling molecule in pulmonary vessels. Nitric oxide (NO) can moderate pulmonary hypertension caused by elevation of the pulmonary arterial pressure. Inhaling low concentrations of nitric oxide (NO), for example, in the range of 20-100 ppm can rapidly and safely decrease pulmonary hypertension in a mammal by vasodilation of pulmonary vessels.

Some disorders or physiological conditions can be mediated by inhalation of nitric oxide (NO). The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia. Typically, the NO gas is supplied in a bottled gaseous form diluted in nitrogen gas (N₂). Great care has to be taken to prevent the presence of even trace amounts of oxygen (O₂) in the tank of NO gas because the NO, in the presence of O₂, is oxidized to nitrogen dioxide (NO₂). Unlike NO, the part per million levels of NO₂ gas is highly toxic if inhaled and can form nitric and nitrous acid in the lungs.

SUMMARY

In one general aspect, an apparatus for converting nitrogen dioxide to nitric oxide includes a receptacle. The receptacle includes an inlet, an outlet, and a surface-active material coated with an aqueous solution of an antioxidant. The inlet is configured to receive a gas flow and fluidly communicate the gas flow to the outlet through the surface-active material such that nitrogen dioxide in the gas flow is converted to nitric oxide.

Implementations may include one or more of the following features. For example, the antioxidant may be ascorbic acid, alpha tocopherol or gamma tocopherol. The surface-active material may be saturated with the aqueous solution of the antioxidant. The surface-active material may include a substrate that retains water, such as a silica gel. The silica gel may be 35 to 70 sized mesh. The receptacle may be a cartridge and may be at ambient temperature.

The surface-active material may be prepared using a solution of ascorbic acid in water. The solution may be, for example, a 20% solution of ascorbic acid in water, a 25% solution of ascorbic acid in water, or a 30% solution of ascorbic acid in water. The surface-active material may be prepared by soaking the surface-active material in a solution of ascorbic acid in water, and air drying the surface-active material, or drying the surface-active material with a gas, before inserting the surface-active material into the receptacle.

The receptacle may include screen and glass wool adjacent to both the inlet and the outlet. The screen and glass wool may be soaked in the aqueous solution of antioxidant before being inserted in the receptacle.

In another general aspect, an apparatus for generating a therapeutic gas including nitric oxide for use in delivering the therapeutic gas to a mammal includes a permeation cell and a receptacle. The permeation cell has liquid nitrogen dioxide and is capable of diffusing gaseous nitrogen dioxide into an air flow. The receptacle includes an inlet, an outlet, and a surface-active material coated with an aqueous solution of an antioxidant. The inlet is configured to receive the air flow from the permeation cell and fluidly communicate the air to flow to the outlet through the surface-active material coated with an aqueous solution of antioxidant to convert the gaseous nitrogen dioxide to nitric oxide at ambient temperature.

Implementations may include one or more of the features noted above and one or more of the following features. For example, an air pump capable of generating an air flow may be included, and the permeation cell may be configured to receive the air flow generated by the air pump. The air pump may be portable. An oxygen-enrichment device capable of supplying oxygen in an air flow may be included, and the permeation cell may be configured to received the air flow enriched by the oxygen-enrichment device.

The receptacle may be a first receptacle and a second receptacle may be included. The second receptacle may include a second inlet, a second outlet, and a second surface-active material coated with an aqueous solution of an antioxidant. The second inlet is configured to receive the air flow from the first receptacle and fluidly communicate the air flow to the second outlet through the second surface-active material coated with an aqueous solution of antioxidant to convert the gaseous nitrogen dioxide to nitric oxide at ambient temperature. A flexible bag operable to inflate and deflate as the mammal breathes may be included, and the second receptacle may be positioned between the flexible bag and a point at which the air flow having the nitric oxide is delivered to the mammal.

Instead of the surface-active material and antioxidant, the second receptacle may include a second inlet, a second outlet, and activated alumina. The second inlet may be configured to receive the air flow from the first receptacle and fluidly communicate the air flow to the second outlet through the activated alumina to trap the gaseous nitrogen dioxide at ambient temperature.

Other features will be apparent from the following description, including the drawings, and the claims.

DETAILED DESCRIPTION

When delivering nitric oxide (NO) for therapeutic use to a mammal, it can be important to avoid delivery of nitrogen dioxide ($NO_2$) to the mammal. Nitrogen dioxide ($NO_2$) can be formed by the oxidation of nitric oxide (NO) with oxygen ($O_2$). The rate of formation of nitrogen dioxide ($NO_2$) is proportional to the oxygen ($O_2$) concentration multiplied by the square of the nitric oxide (NO) concentration—that is, $(O_2)*(NO)*(NO)=NO_2$.

A NO delivery system that converts nitrogen dioxide ($NO_2$) to nitric oxide (NO) is provided. The system employs an surface-active material coated with an aqueous solution of antioxidant as a simple and effective mechanism for making the conversion. More particularly, $NO_2$ can be converted to NO by passing the dilute gaseous $NO_2$ over a surface-active material coated with an aqueous solution of antioxidant. When the aqueous antioxidant is ascorbic acid (that is, vitamin C), the reaction is quantitative at ambient temperatures. The techniques employed by the system should be contrasted for other techniques for converting $NO_2$ to NO. Two such techniques are to heat a gas flow containing $NO_2$ to over 650 degrees Celsius over stainless steel, or 450 degrees Celsius over Molybdenum. Both of these two techniques are used in air pollution instruments that convert $NO_2$ in air to NO, and then measure the NO concentration by chemiluminescence. Another method that has been described is to use silver as a catalyst at temperatures of 160 degrees Celsius to over 300 degrees Celsius.

One example of a surface-active material is silica gel. Another example of a surface-active material that could be used is cotton. The surface-active material may be or may include a substrate capable of retaining water. Another type of surface-active material that has a large surface area that is capable of absorbing moisture also may be used.

Figure 1:
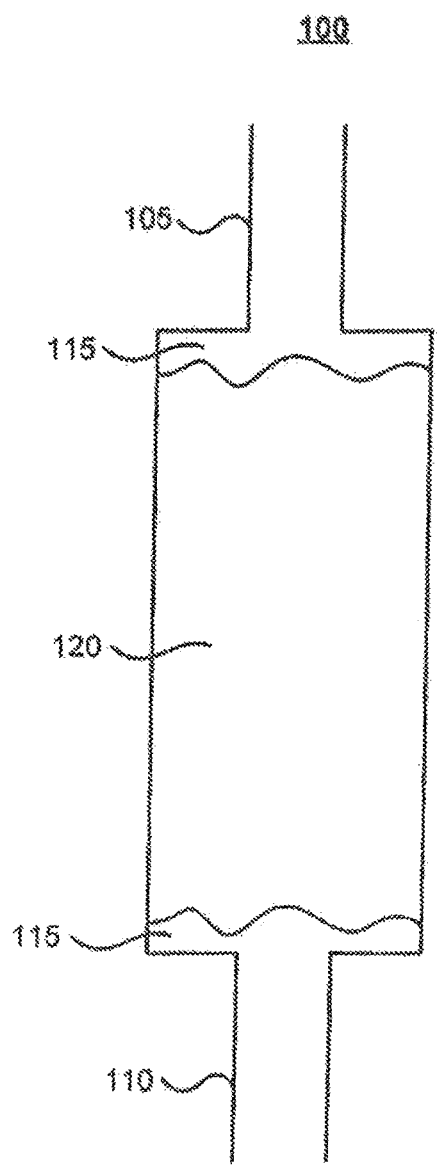
FIG. 1 is a block diagram of a cartridge that converts $NO_2$ to NO.

FIG. 1 illustrates a cartridge 100 for generating NO by converting $NO_2$ to NO. The cartridge 100, which may be referred to as a NO generation cartridge, a GENO cartridge, or a GENO cylinder, includes an inlet 105 and an outlet 110. Screen and glass wool 115 are located at both the inlet 105 and the outlet 110, and the remainder of the cartridge 100 is filled with a surface-active material 120 that is soaked with a saturated solution of antioxidant in water to coat the surface-active material. The screen and glass wool 115 also is soaked with the saturated solution of antioxidant in water before being inserted into the cartridge 100. In the example of FIG. 1, the antioxidant is ascorbic acid.

In a general process for converting $NO_2$ to NO, an air flow having $NO_2$ is received through the inlet 105 and the air flow is fluidly communicated to the outlet 110 through the surface-active material 120 coated with the aqueous antioxidant. As long as the surface-active material remains moist and the antioxidant has not been used up in the conversion, the general process is effective at converting $NO_2$ to NO at ambient temperature.

Figure 2:
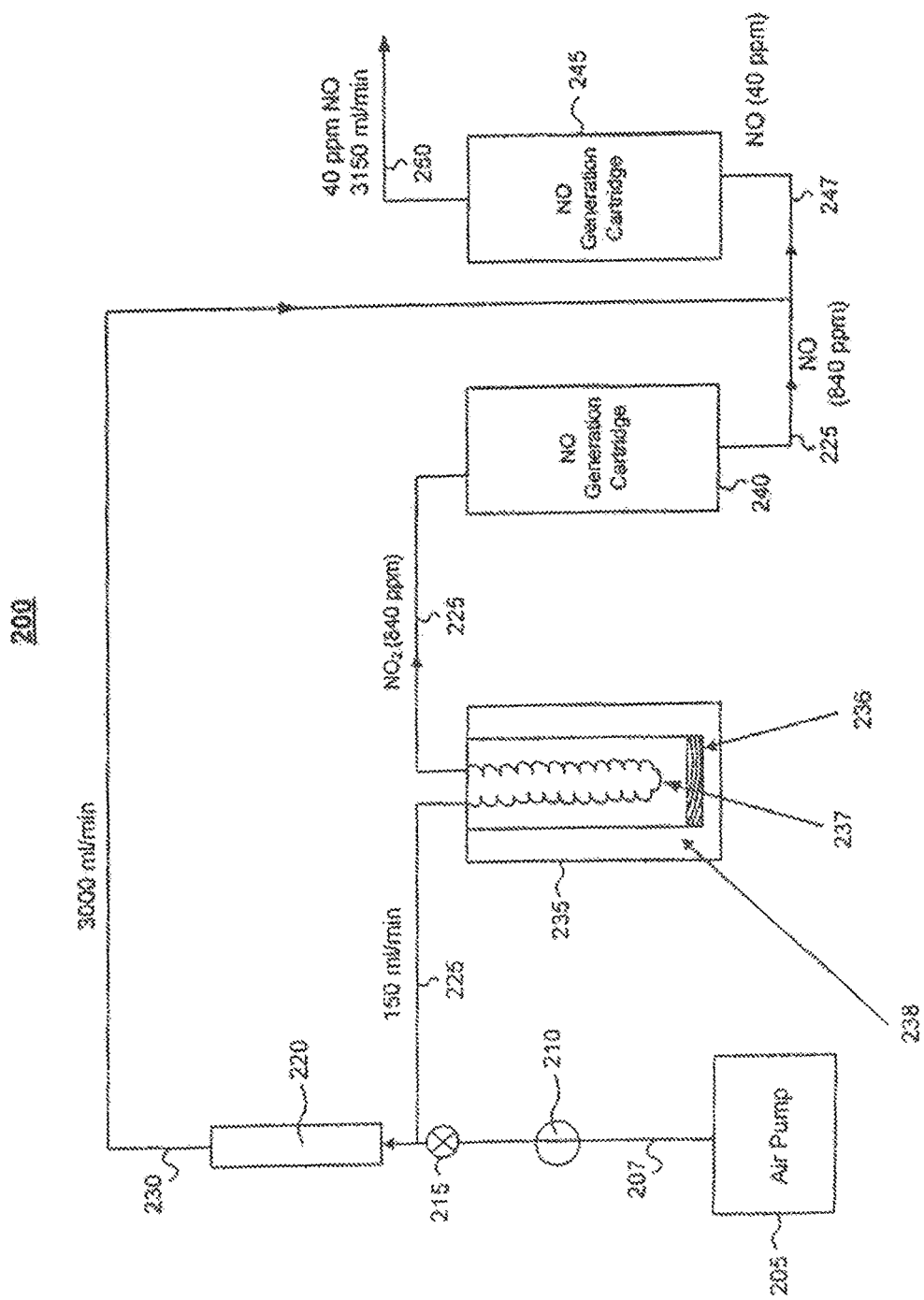
FIGS. 2-10 are block diagrams of NO delivery systems using the cartridge of FIG. 1.

The inlet 105 may receive the air flow having $NO_2$ from an air pump that fluidly communicates an air flow over a permeation tube containing liquid $NO_2$, such as in the system 200 of FIG. 2. The inlet 105 also may receive the air flow having $NO_2$, for example, from a pressurized bottle of $NO_2$, which also may be referred to as a tank of $NO_2$. The inlet 105 also may receive an air flow with $NO_2$ in nitrogen ($N_2$), air, or oxygen ($O_2$). The conversion occurs over a wide concentration range. Experiments have been carried out at concentrations in air of from about 2 ppm $NO_2$ to 100 ppm $NO_2$, and even to over 1000 ppm $NO_2$. In one example, a cartridge that was approximately 6 inches long and had a diameter of 1.5-inches was packed with silica gel that had first been soaked in a saturated aqueous solution of ascorbic acid. The moist silica gel was prepared using ascorbic acid (i.e., vitamin C) designated as A.C.S reagent grade 99.1% pure from Aldrich Chemical Company and silica gel from Fischer Scientific International, Inc., designated as S8 32-1, 40 of Grade of 35 to 70 sized mesh. Other sizes of silica gel also are effective. For example, silica gel having an eighth-inch diameter also would work.

The silica gel was moistened with a saturated solution of ascorbic acid that had been prepared by mixing 35% by weight ascorbic acid in water, stirring, and straining the water/ascorbic acid mixture through the silica gel, followed by draining. It has been found that the conversion of $NO_2$ to NO proceeds well when the silica gel coated with ascorbic acid is moist. The conversion of $NO_2$ to NO does not proceed well in an aqueous solution of ascorbic acid alone.

The cartridge filled with the wet silica gel/ascorbic acid was able to convert 1000 ppm of $NO_2$ in air to NO at a flow rate of 150 ml per minute, quantitatively, non-stop for over 12 days. A wide variety of flow rates and $NO_2$ concentrations have been successfully tested, ranging from only a few ml per minute to flow rates of up to 5,000 ml per minute. The reaction also proceeds using other common antioxidants, such as variants of vitamin E (e.g., alpha tocopherol and gamma tocopherol).

The antioxidant/surface-active material GENO cartridge may be used for inhalation therapy. In one such example, the GENO cartridge may be used as a $NO_2$ scrubber for NO inhalation therapy that delivers NO from a pressurized bottle source. The GENO cartridge may be used to remove any $NO_2$ that chemically forms during inhalation therapy. This GENO cartridge may be used to help ensure that no harmful levels of $NO_2$ are inadvertently inhaled by the patient.

First, the GENO cartridge may be used to supplement or replace some or all of the safety devices used during inhalation therapy in conventional NO inhalation therapy. For example, one type of safety device warns of the presence of $NO_2$ in air when the concentration of $NO_2$ exceeds a preset or predetermined limit, usually 1 part per million or greater of $NO_2$. Such a safety device may be unnecessary when a GENO cartridge is positioned in a NO delivery system just prior to the patient breathing the NO laden air. The GENO cartridge converts any $NO_2$ to NO just prior to the patient breathing the NO laden air, making a device to warn of the presence of $NO_2$ in air unnecessary.

Furthermore, a GENO cartridge placed near the exit of inhalation equipment and gas plumbing lines (which also may be referred to as tubing) also reduces or eliminates problems associated with formation of $NO_2$ that occur due to transit times in the ventilation equipment. As such, use of the GENO cartridge reduces or eliminates the need to ensure the rapid transit of the gas through the gas plumbing lines that is needed in conventional applications.

Alternatively or additionally, a $NO_2$ removal cartridge can be inserted just before the attachment of the delivery system to the patient to further enhance safety and help ensure that all traces of the toxic $NO_2$ have been removed. The $NO_2$ removal cartridge may be a GENO cartridge used to remove any trace amounts of $NO_2$. Alternatively, the $NO_2$ removal cartridge may include heat-activated alumina. A cartridge with heat-activated alumina, such as supplied by Fisher Scientific International, Inc., designated as A505-212, of 8-14 sized mesh is effective at removing low levels of $NO_2$ from an air or oxygen stream, and yet lets NO gas pass through without loss. Activated alumina, and other high surface area materials like it, can be used to scrub $NO_2$ from a NO inhalation line.

In another example, the GENO cartridge may be used to generate NO for therapeutic gas delivery. Because of the effectiveness of the NO generation cartridge in converting toxic $NO_2$ to NO at ambient temperatures, liquid $NO_2$ can be used as the source of the NO. When liquid $NO_2$ is used as a source for generation of NO, there is no need for a pressurized gas bottle to provide NO gas to the delivery system. An example of such a delivery system is described in more detail with respect to FIG. 2. By eliminating the need for a pressurized gas bottle to provide NO, the delivery system may be simplified as compared with a conventional apparatus that is used to deliver NO gas to a patient from a pressurized gas bottle of NO gas. A NO delivery system that does not use pressurized gas bottles may be more portable than conventional systems that rely on pressurized gas bottles.

FIGS. 2-14 illustrate techniques using silica gel as the surface-active material employed in a GENO cartridge. As discussed previously, silica gel is only one example of a surface-active material that may be used in a NO generation system or cartridge.

FIG. 2 illustrates a NO generation system 200 that converts liquid $NO_2$ to NO gas, which then may be delivered to a patient for NO inhalation therapy. In general, a flow of air generated by an air pump 205 is passed through a gas permeation cell 235 having liquid $NO_2$ and its dimer $N_2O_4$ (collectively, 236). The air flow exiting the gas permeation cell 235 includes gaseous $NO_2$, which is converted to NO gas by a NO generation cartridge 240. The NO gas mixture may be delivered to a patient for inhalation therapy, for example, using a mask, a cannula, or a ventilator. The concentration of NO in the NO gas mixture delivered to the patent may be controlled by controlling the temperature of the gas permeation cell 235 or the air flow rate through the flow meter 220.

More particularly, the system 200 includes an air pump 205, a regulator 210, a flow diverter 215 and a flow meter 220. The system is configured such that air flow 207 from the air pump 205 is divided into a first flow 225 of 150 ml/min and a second flow 230 of 3000 ml/min. The air flow 207 may be dry or moist.

The flow 225 is passed through a gas permeation cell 235 containing liquid $NO_2$ and its dimer $N_2O_4$ (collectively, 236) and a gas permeation tube 237. The permeation cell 235 also may be referred to as a permeation generator, a permeation device or a permeation tube holder. The $NO_2$ diffuses through the gas porous membrane of the gas permeation cell 235 into the flow 225. In one example, the flow 225 of 150 ml/min of air is allowed to flow through the permeation tube 237, such as a permeation tube supplied by KinTek Corporation of Austin, Tex. The permeation tube 237 is designed to release $NO_2$ at a steady rate such that the gas stream leaving the permeation tube in the flow 225 contains about 840 ppm of $NO_2$ when the permeation tube 237 is at a temperature of 40 degrees Celsius. The region 238 is temperature controlled to maintain a temperature of approximately 40 degrees Celsius. As discussed more fully below, maintaining the temperature of the permeation cell 235 helps to control the concentration of NO delivered to the patient.

The 150 ml of air containing 840 ppm of $NO_2$ then flows through a NO generation cartridge 240. In this example, the NO generation cartridge 240 is 6 inches long with a diameter of 1.5 inches and contains moist ascorbic acid on silica gel, which serves as the conversion reagent. The NO generation cartridge 240 may be an implementation of cartridge 100 of FIG. 1. The air stream 225 exiting from the NO generation cartridge 240 contains 840 ppm of NO, with all or essentially all of the $NO_2$ having been converted to NO.

The 225 flow of 150 ml/min with 840 ppm NO then mixes with the flow 230 of 3000 ml/min of air or oxygen to produce a flow 247 of 3150 ml/min containing 40 ppm of NO. After mixing, the flow 247 passes through a second NO generation cartridge 245 to remove any $NO_2$ that may have been formed during the dilution of NO when the flows 225 and 230 were mixed. The NO generation cartridges 240 and 245 may be sized the same, though this need not necessarily be so. For example, the NO generation cartridge 245 may be sized to have a smaller $NO_2$ conversion capacity than the NO generation cartridge 240. The resulting flow 250 of air having NO is then ready for delivery to the patient. The system 200 may be designed to produce a steady flow of NO gas for a period as short as a few hours or as long as 14 days or more. In one test, the system 200 was shown to deliver a steady flow of 40 ppm NO gas in air, without $NO_2$, for over 12 days, where the NO and $NO_2$ concentrations were measured by a chemiluminescent gas analyzer.

As an alternative to the system 200, a NO generation system may include a permeation tube that has a larger flow capacity than the permeation tube 237. In such a case, the larger permeation tube may be able to process all of the inhaled air needed to be delivered to the patient so that, for example, the flow 230 and the conversion tube 245 are not necessary.

The system 200 can be made portable, for example, if the air pump 205 used to supply the air is a portable air pump, such as a simple oil free pump. If oxygen-enriched air is needed by the patient, oxygen can be supplied in addition to, or in lieu of, the air supplied by the air pump 205. Oxygen can be supplied, for example, from an oxygen tank or a commercially available oxygen generator. Oxygen also can be supplied from a tank that has $NO_2$ mixed with $O_2$.

In some implementations, the permeation cell 238 and/or the two conversion cartridges 240 and 245 may be disposable items.

The concentration of NO in the flow 250 exiting the system 200 is independent of the flow 225 through the permeation cell 235, as long as the flow 225 is greater than a few milliliters per minute. The concentration of NO in the flow 250 is a function of the temperature of the permeation cell 235 and to a lesser degree the air flow rate 230. For example, with a constant air flow rate 230, the system 200 is designed to deliver 40 ppm NO at a temperature of 40 degrees Celsius; however, the concentration of NO can be reduced to 20 ppm NO at 30 degrees Celsius and increased to 80 ppm NO at 50 degrees Celsius. As such, a temperature controller can be used to adjust the concentration of the NO gas to be delivered. Once the desired NO concentration is selected and the temperature controller is set to maintain the particular temperature to deliver the desired concentration, the delivery rate of NO gas at the desired concentration remains constant. One example of a temperature controller is an oven, such as an oven available from KinTek Corporation, in which the permeation tube is placed. Another example of a temperature controller is a beaker of de-ionized water placed on a hot plate where the permeation tube is placed in the beaker. A thermometer may also be placed in the beaker to monitor the temperature of the water.

The NO generation system can be used to deliver a steady flow of NO gas mixture for use with a cannula, with the excess gas being vented to the environment. The NO generation system can be used with a ventilator, and, in such a case, the delivery from the NO generator must remain steady and cannot be shut off without endangering the patient receiving the NO. To handle the increased flow necessary during the air intake to the patient, the NO gas mixture may be used to inflate and then deflate a flexible bag. If the air flow to the patient is delayed in any way, a NO generation cartridge can be inserted in the NO generation system at the point immediately prior to inhalation to remove any $NO_2$ that may form from NO reacting with $O_2$ during such a delay. This helps to ensure that even very small amounts of $NO_2$ that may be formed in the bag during the delay are removed prior to the therapeutic gas flow being inhaled by the patient.

A detector can be included in the therapeutic gas delivery system 200 to detect the concentration of NO in the therapeutic gas stream. The detector can also detect the concentration of $NO_2$ in the therapeutic gas, if necessary, and may provide a warning if the NO concentration is outside a predetermined range or if the concentration of $NO_2$ is above a threshold value. Examples of monitoring techniques include chemiluminescence and electrochemical techniques. The presence of nitric oxide can be detected by, for example, a chemiluminescence detector.

Figure 3:
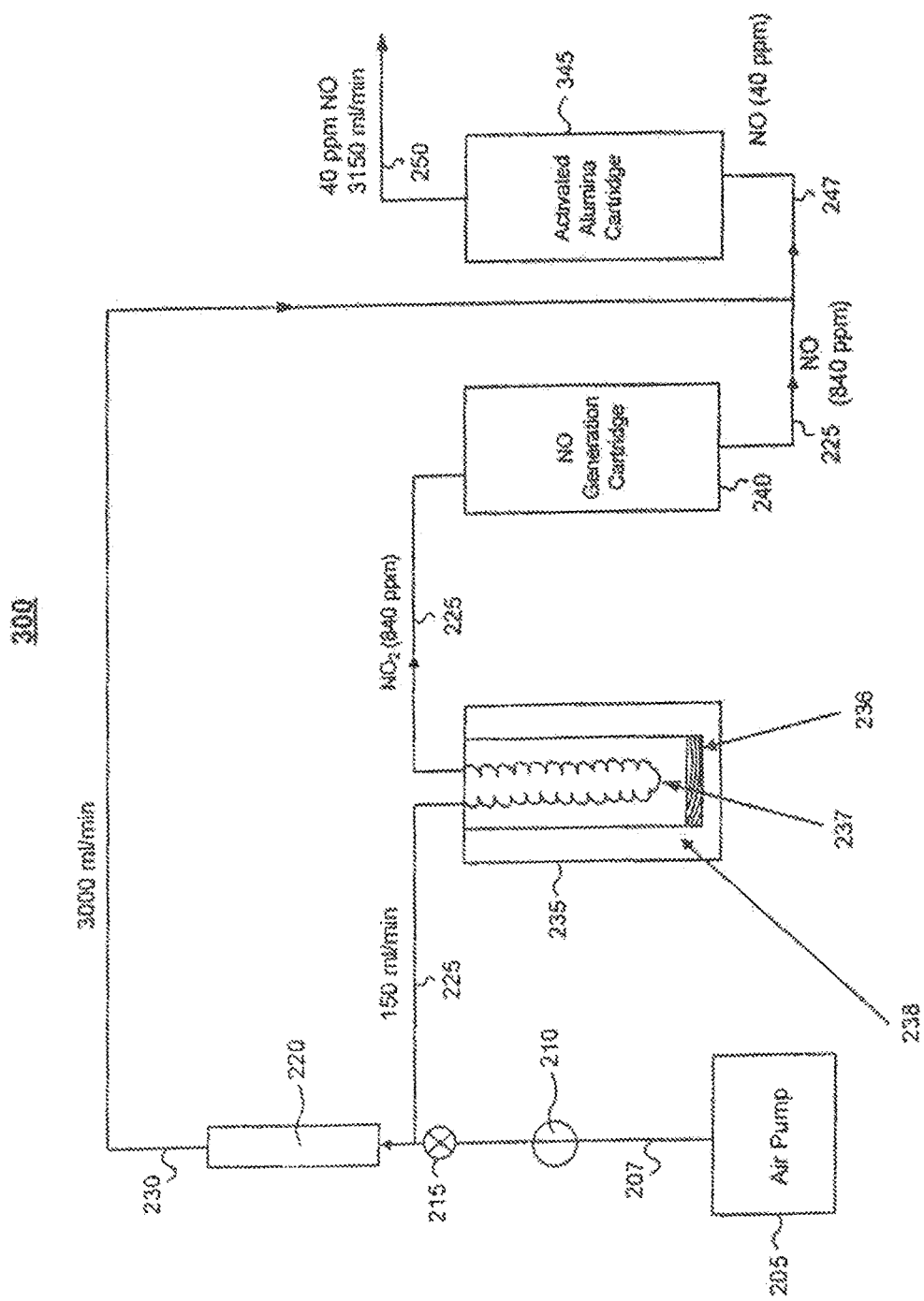

FIG. 3 depicts a NO generation system 300 that converts liquid $NO_2$ to NO gas, which then may be delivered to a patient for NO inhalation therapy. In contrast to the NO generation system 200 of FIG. 2, the NO generation system 300 includes an activated alumina cartridge 345. The activated alumina cartridge 345 removes any $NO_2$ that forms during a delay. In contrast to the NO generation cartridge 240, which removes the $NO_2$ by converting the $NO_2$ to NO, and thereby quantitatively recovering the $NO_2$, the activated alumina cartridge 345 removes $NO_2$ from the process gas stream without generating NO.

Figure 4:
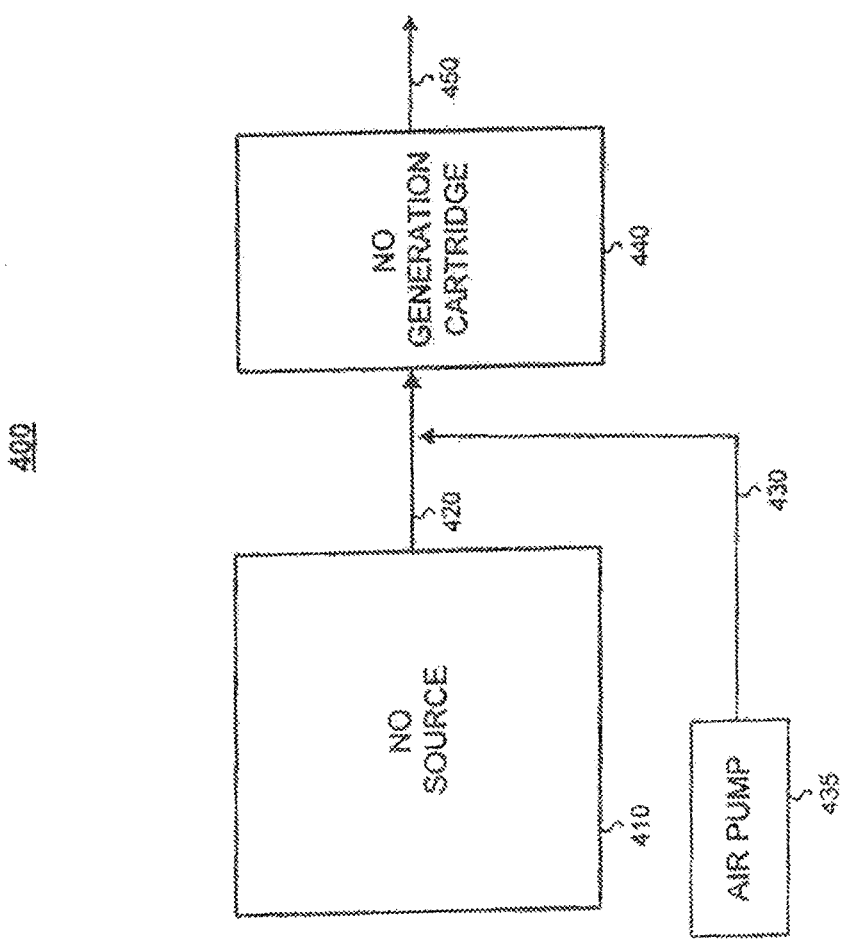

FIG. 4 illustrates a therapeutic gas delivery system 400 that uses a NO generation cartridge 440, which may be an implementation of NO generation cartridge 100 of FIG. 1. The system 400 uses a NO source 410 to provide gaseous NO in a flow 420 through tubing. In one example, the NO source 410 may be a pressurized bottle of NO. A flow of air 430 through the tubing is generated by an air pump 435 and is mixed with the flow 420. The air flow entering the NO generation cartridge 440 includes gaseous NO. Any $NO_2$ gas that may have formed in flow 420 is removed by the NO generation cartridge 440. The air flow 450 exiting the NO generation cartridge 440 includes therapeutic NO gas but is devoid of toxic levels of $NO_2$. The air flow 450 then may be delivered to a patient for NO inhalation therapy.

Figure 5:
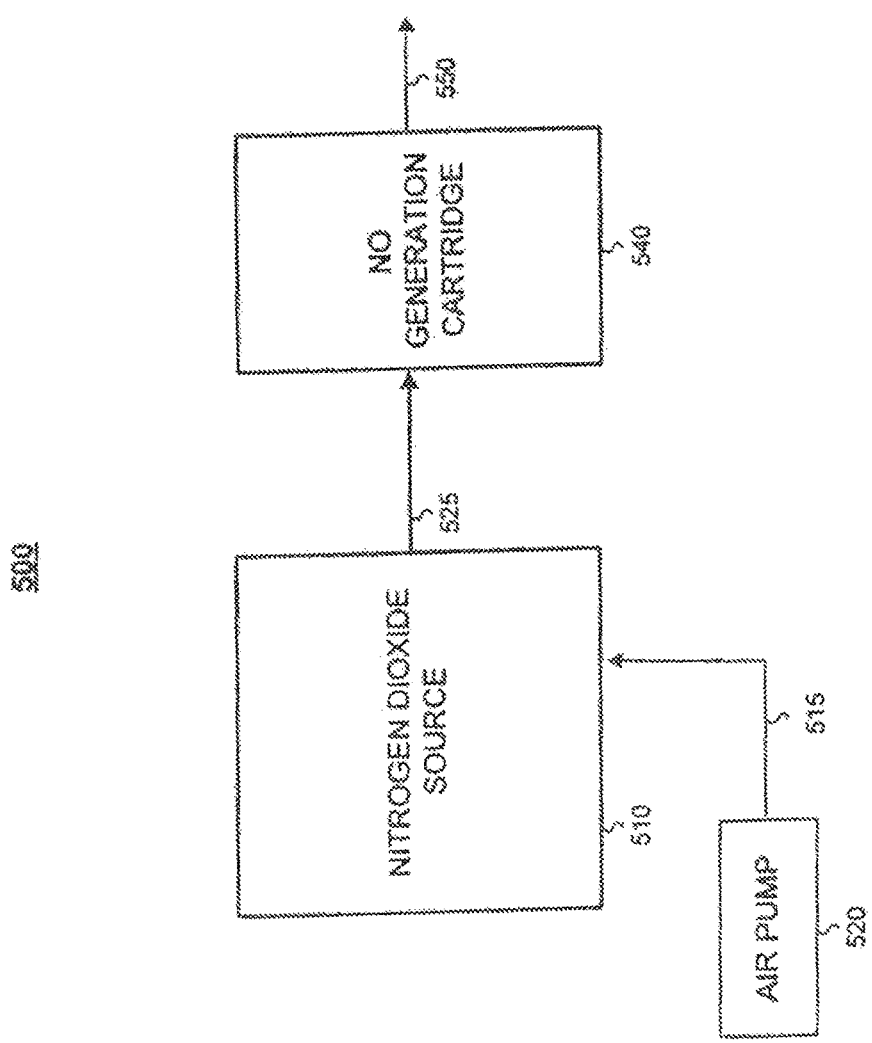

FIG. 5 illustrates a therapeutic gas delivery system 500 that uses a NO generation cartridge 540, which may be an implementation of NO generation cartridge 100 of FIG. 1. In contrast to therapeutic gas delivery system 400 of FIG. 4, the system 500 generates NO from a $NO_2$ source 510. The $NO_2$ source 510 may use diffuse liquid $NO_2$ in an air flow 515 generated by an air pump 520 such that the flow 525 exiting the $NO_2$ source 510 includes gaseous $NO_2$. In some implementations, $NO_2$ source 510 may be a pressurized bottle of $NO_2$.

In any case, the air flow 525 entering the NO generation cartridge 440 includes gaseous $NO_2$. The NO generation cartridge 440 converts the $NO_2$ gas in flow 525 to NO. The air flow 550 exiting the NO generation cartridge 540 includes therapeutic NO gas but is devoid or essentially devoid of $NO_2$. The air flow 550 then may be delivered to a patient for NO inhalation therapy.

Figure 6:
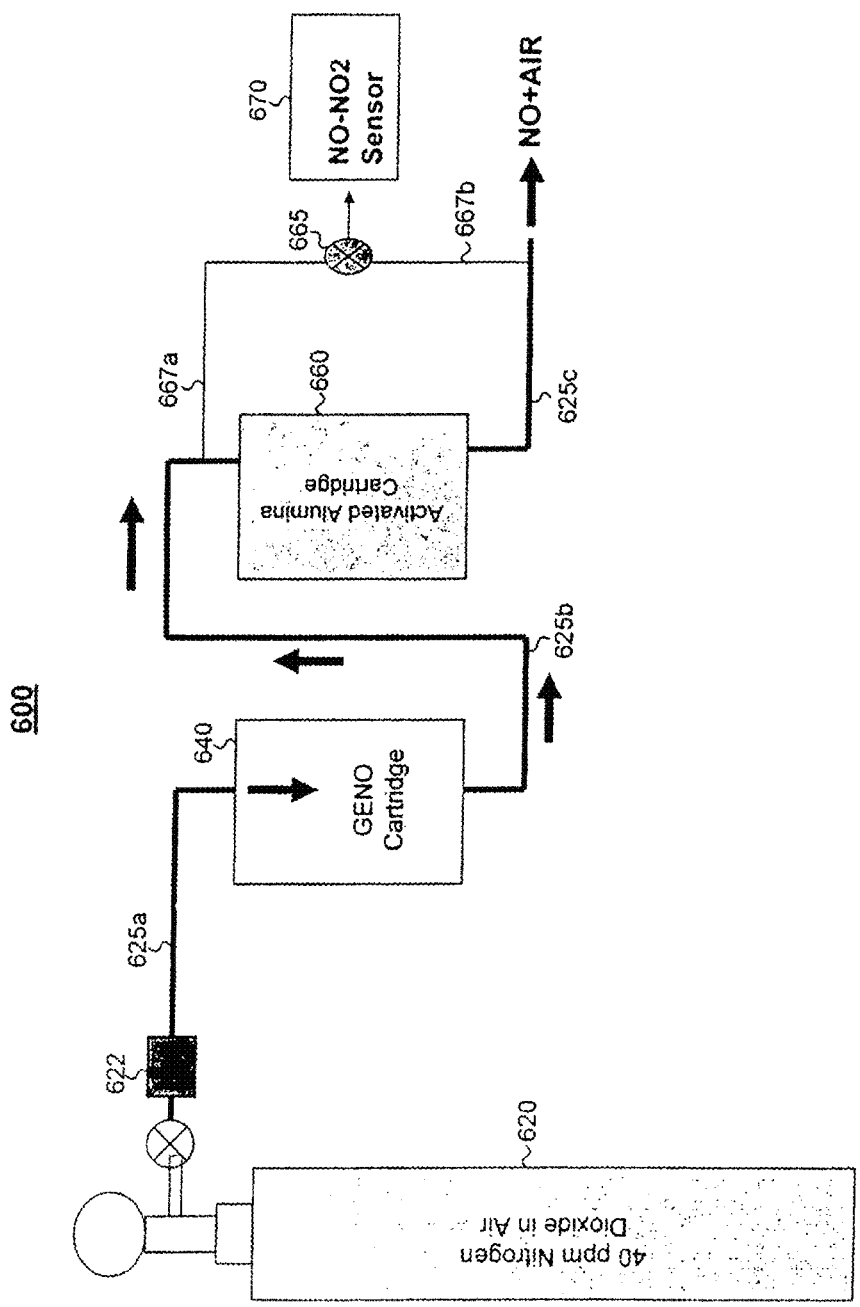

FIG. 6 illustrates a GENO pressure tank system 600 for delivering therapeutic gas. The system 600 includes a tank 620 having 40 ppm $NO_2$ in air, which is commercially available, and a flow controller 622. In one example of tank 620, a 300 cu. ft. tank lasts 1.2 days at an air flow of 5 L/min.

An air flow 625a of $NO_2$ in air exits the flow controller 622 and enters a GENO cartridge 640. The GENO cartridge 640 uses the $NO_2$ as a precursor and converts the $NO_2$ to NO. The air flow 625b exiting the GENO cartridge 640 includes therapeutic NO gas. The air flow 625b enters an activated alumina cartridge 660 to remove any $NO_2$ in the air flow 625b. The air flow 625c that exits the activated alumina cartridge 660 is delivered to a patient for NO inhalation therapy.

The system 600 includes a NOx sample valve 665 and a NO—$NO_2$ sensor 670 operable to detect $NO_2$. A NO—$NO_2$ sensor also may be referred to as a NO—$NO_2$ detector. The NOx sample valve 665 is operable to provide air samples from air flows 667a and 667b to the NO—$NO_2$ sensor 670. Using the NO—$NO_2$ detector 670 to detect the presence of any $NO_2$ in air flow 667a may provide an indication of a failure of the GENO cartridge 640, and, as such, provides a prudent safeguard to ensure that no toxic $NO_2$ is delivered to the patient.

In some implementations, the activated alumina cartridge 660 may be replaced with a GENO cartridge.

Figure 7:
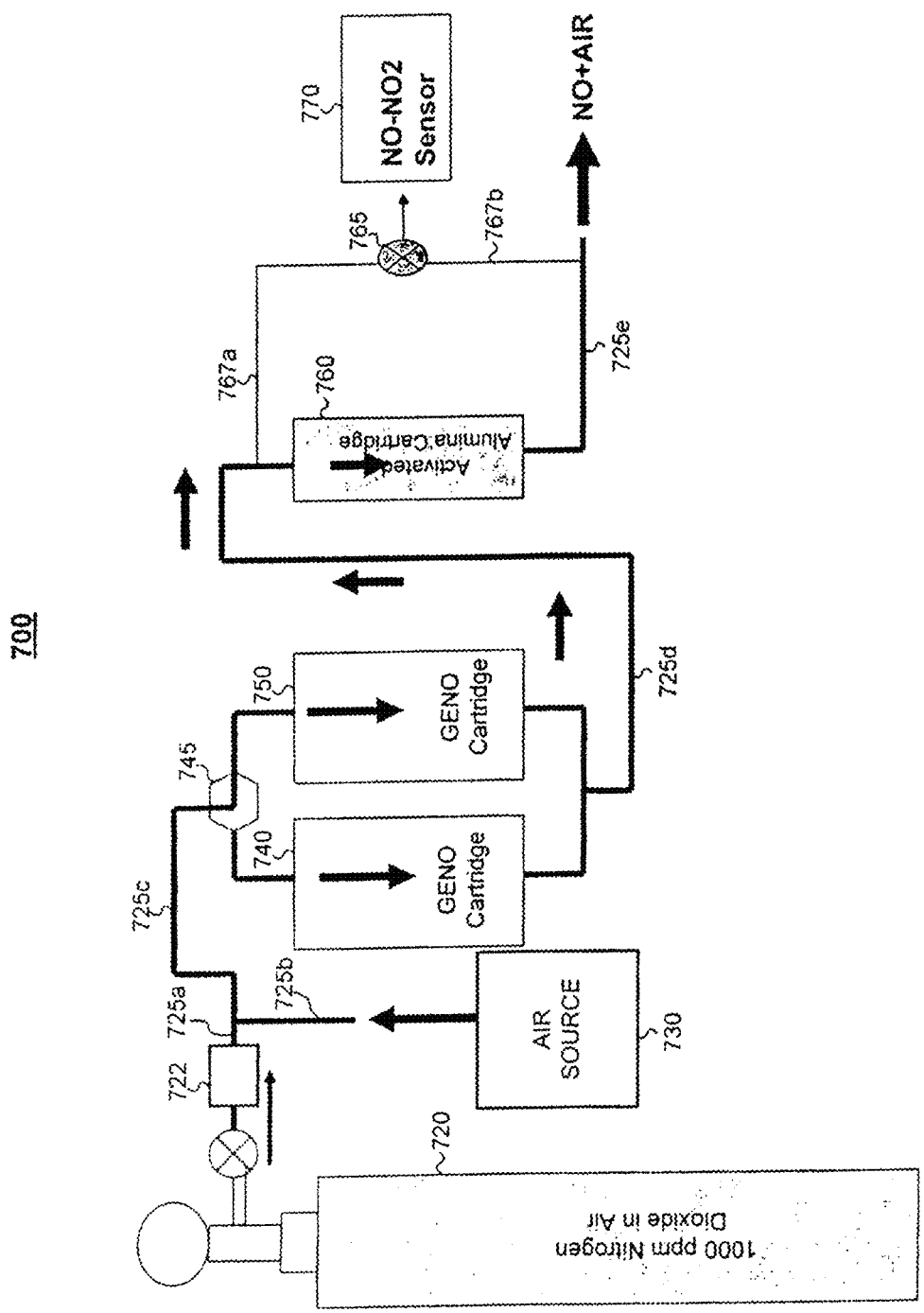

FIG. 7 illustrates a GENO high-concentration $NO_2$ pressure system 700 for delivering therapeutic gas. In contrast to the system 600 of FIG. 6, the system 700 includes two GENO cartridges 740 and 750 and a switching valve 745 to control which of the GENO cartridges 740 or 750 is used. When a NO—$NO_2$ detector 770 detects the presence of $NO_2$ in the air flow 725d exiting the GENO cartridge being used, the switching valve 745 can be manipulated to switch the air flow 725c to pass through the other GENO cartridge 740 or 750. The ability to switch to a second GENO cartridge in the event of failure of a first GENO cartridge provides an additional layer of safety for the patient to whom the therapeutic gas is being delivered.

More particularly, the system 700 includes a tank 720 having 1000 ppm $NO_2$ in air and a flow controller 722. In the example, the tank 720 is a 150 cu. ft. tank at 2250 psi and provides an air flow of 125 cc/min. At an air flow of 5 L/min of 40 ppm delivered to the patient, the tank 720 lasts approximately 23 days. The tank 720 is able to provide an air flow for a longer period than the expected life of each GENO cartridge 740 and 750, which is, in the cartridge used in this example, less than two weeks. As such, the ability to switch from one GENO cartridge to another GENO cartridge helps to ensure that the contents of the tank are used or substantially used.

An air flow 725a of $NO_2$ in air exits the flow controller 722 and is mixed with an air flow 725b of 5 L/min that is generated by an air source 730, such as an air pump. The resulting air flow 725*c* enters the switching valve 745. The switching valve 745 controls which of the GENO cartridges 740 or 750 receives the air flow 725*c*. As shown, the switching valve 745 is set such that the air flow 725*c* is provided to the GENO cartridge 750. The GENO cartridge 750 converts the $NO_2$ in the air flow 725*c* to NO. The air flow 725*d* exiting the GENO cartridge 725*d* includes therapeutic NO gas. The air flow 725*d* enters an activated alumina cartridge 760 to remove any $NO_2$ in the air flow 725*d*. The air flow 725*e* that exits the activated alumina cartridge 760 is delivered to a patient for NO inhalation therapy.

The system 700 includes a NO sample valve 765 and an $NO-NO_2$ sensor 770 operable to detect $NO_2$. The NO sample valve 765 is operable to provide air samples from air flows 767*a* and 767*b* to the $NO-NO_2$ sensor 770. Using the $NO-NO_2$ sensor 770 to detect the presence of any $NO_2$ in air flow 767*a* may provide an indication of a failure of the GENO cartridge being used so that the second GENO cartridge may be used. In some implementations, the activated alumina cartridge 760 may be replaced with a GENO cartridge.

Figure 8:
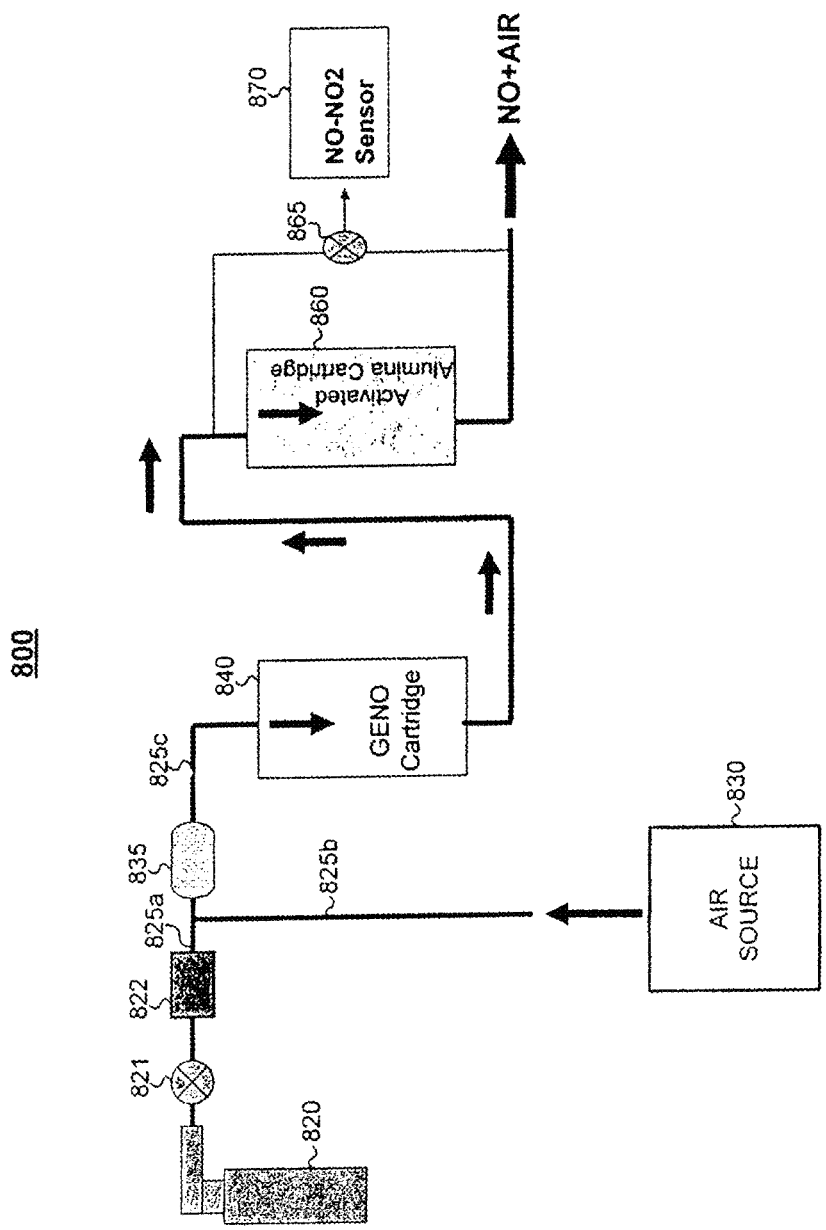

FIG. 8 illustrates a GENO high-concentration $NO_2$ cartridge system 800 for delivering therapeutic gas. In contrast to the systems 600 or 700 of FIGS. 6 and 7, respectively, the system 800 includes a high-concentration $NO_2$ cartridge as the source of the $NO_2$ used to generate the NO. More particularly, the system 800 includes an $NO_2$ cartridge 800, such as a small butane tank or a cartridge conventionally used to deliver $CO_2$. In one example of the system 800, a $NO_2$ cartridge with dimensions of 1 inch by 6 inches and filled with 5% $NO_2$ in $CO_2$ was able to deliver $NO_2$ for 14 days.

A $NO_2$ shut-off valve 821 is adjacent to the cartridge 800 to shut-off delivery of $NO_2$ from the cartridge 800. The system 800 also includes a flow controller 822 to ensure a generally constant flow rate of the flow 825*a* exiting the flow controller 822. The flow controller 822 is a glass tube with a small hole through which the gas flow 825*a* passes. In various implementations of the system 800, the flow controller 822 may ensure a constant flow rate of 1 to 10 cc/min.

The gas flow 825*a* having $NO_2$ exits the flow controller 822 and is mixed with an air flow 825*b* of approximately 5 L/min that is generated by an air source 830. A gas mixer 835 ensures that the air flows 825*a* and 825*b* are fully (or essentially fully) mixed. The resulting air flow 825*c* with $NO_2$ enters a GENO cartridge 840 that generates NO.

The system 800 also includes an activated alumina cartridge 860 to remove any $NO_2$ before the therapeutic gas including NO is delivered to the patient at the rate of approximately 5 L/min. The system 800 includes a $NO_x$ sample valve 865 and a $NO-NO_2$ sensor 870 operable to detect $NO_2$. In some implementations, the activated alumina cartridge 860 may be replaced with a GENO cartridge.

Figure 9:
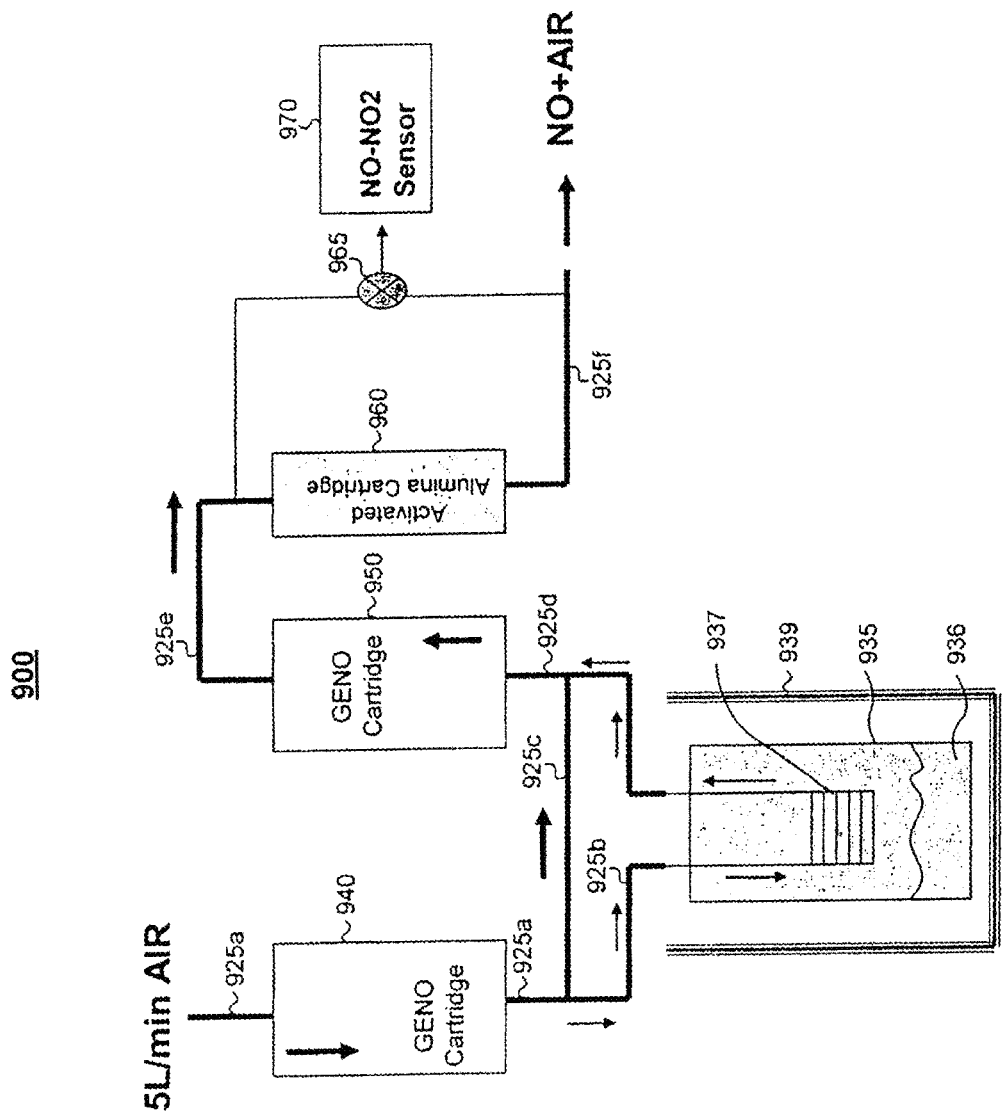

FIG. 9 illustrates a GENO permeation system 900 for delivering therapeutic gas. The system 900 includes an air flow 925*a* of approximately 5 L/min that flows into a GENO cartridge 940, which acts to humidify the air. After exiting the GENO cartridge 940, the air flow 925*a* divides such that an air flow 925*b* passes through a permeation device 935 and an air flow 925*c* does not. The permeation device 935 includes permeation tubing 937 and about 10 cc of liquid $NO_2$ 936 when the air flow 925*a* begins. The permeation device 935 may be an implementation of the permeation cell 235 of FIG. 2. The permeation device 935 is in a permeation oven 939 to maintain a constant, or an essentially constant, temperature to ensure the desired concentration of $NO_2$ is diffused into the air flow 925*b*. The air flow 925*b* and the air flow 925*c* mix to form flow 925*d* before entering the GENO cartridge 950. The GENO cartridge 950 converts the $NO_2$ to NO.

The system 900 also includes an activated alumina cartridge 960 to receive air flow 925*e* and remove any $NO_2$ before the therapeutic gas including NO is delivered to the patient at the rate of approximately 5 L/min. The air flow 925*f* that exits the activated alumina cartridge is delivered to a patient for NO inhalation therapy. The system 900 includes a $NO_x$ sample valve 965 and a $NO-NO_2$ sensor 970 operable to detect $NO_2$.

Figure 10:
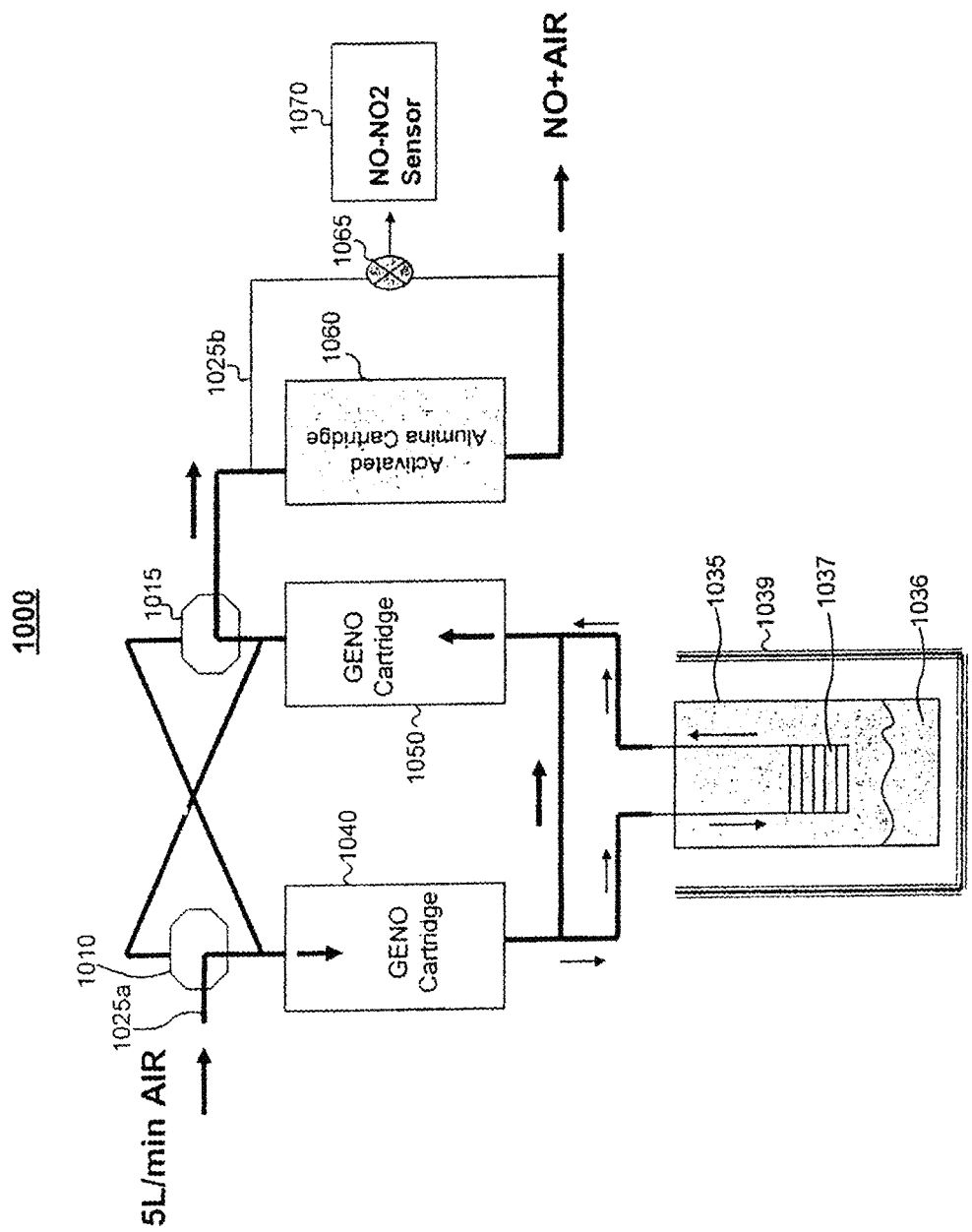

FIG. 10 illustrates a GENO permeation system 1000 for delivering therapeutic gas. In contrast to the system 900 of FIG. 9, the system 1000 includes valves 1010 and 1015 to control which of the GENO cartridges 1040 and 1050 first receives the air flow. The system 1000 uses liquid $NO_2$ in a permeation device 1035 as a source of $NO_2$ to be converted to NO. The system 1000 also includes an activated alumina cartridge 1060 to remove any $NO_2$ before the therapeutic gas including NO is delivered to the patient at the rate of approximately 5 L/min. The system 1000 also includes a NOx sample valve 1065 and a $NO-NO_2$ sensor 1070 operable to detect $NO_2$.

The system 1000 receives an air flow 1025*a* of approximately 5 L/min into the valve 1010, which, together with the valve 1015, controls which of GENO cartridges 1040 or 1050 the air flow 1025*a* first passes through. More particularly, by controlling the position of the valves 1010 and 1015, the air flow 1025*a* can be made to pass through the GENO cartridge 1040, the permeation device 1025, the GENO cartridge 1050, and then the activated alumina cartridge 1060 before being delivered to the patient. By manipulating the position of the valves 1010 and 1015, the air flow 1025*a* also can be made to pass through the GENO cartridge 1050, the permeation device 1025, the GENO cartridge 1040, and then the activated alumina cartridge 1060 before being delivered to the patient.

For example, when the $NO-NO_2$ sensor 1070 detects the presence of $NO_2$ in the air flow 1025*b*, this may signal a need to manipulate the valves 1010 and 1015 to cause the order in which the GENO cartridges 1040 and 1050 are used to be switched—that is, for example, when the air flow 1025*a* flows through the GENO cartridge 1040 before flowing through the GENO cartridge 1050, the values 1010 and 1015 are manipulated to cause the air flow 1025*a* to flow through GENO cartridge 1050 before flowing through the GENO cartridge 1040.

Figure 11:
FIG. 11 is a diagram of another cartridge that converts $NO_2$ to NO.

FIG. 11 illustrates a conceptual design of a GENO cartridge 1100 that converts $NO_2$ to NO. The GENO cartridge 1100 may be an implementation of the cartridge 100 of FIG. 1. The GENO cartridge 1100 is approximately 6-inches long with a 1-inch diameter. The GENO cartridge 1100 includes silica gel saturated with an aqueous solution of ascorbic acid and receives an air flow from an air or oxygen gas bottle containing $NO_2$. The air flow through the cartridge 1100 converts $NO_2$ to NO, which exits the cartridge 1100. The GENO cartridge 1100 works effectively at concentrations of $NO_2$ from 5 ppm to 5000 ppm. The conversion of $NO_2$ to NO using the GENO cartridge 1100 does not require a heat source and may be used at ambient air temperature. The conversion of $NO_2$ to NO using the GENO cartridge 1100 occurs substantially independently of the flow rate of the air flow through the GENO cartridge 1100.

Figure 12:
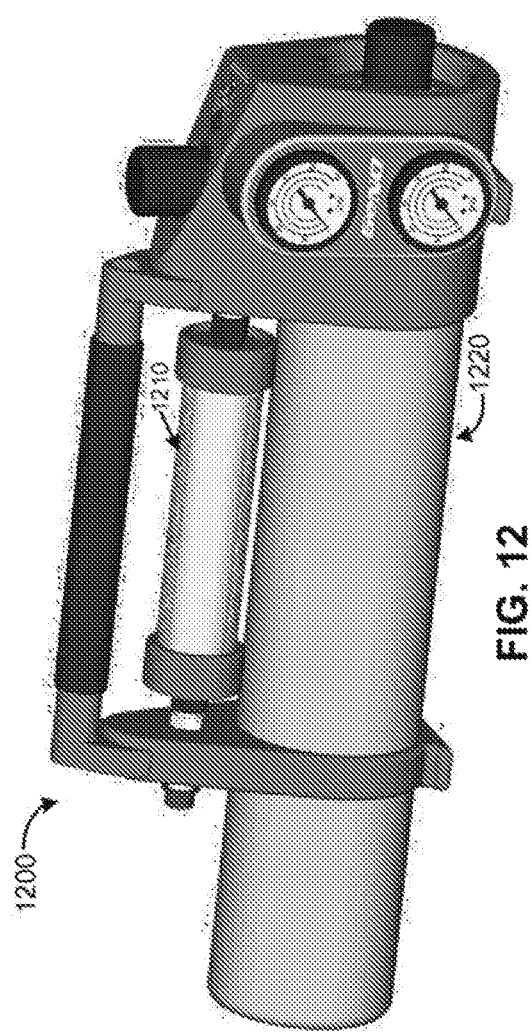
FIGS. 12-14 are diagrams of NO delivery systems using the cartridge of FIG. 11.

FIG. 12 illustrates a therapeutic gas delivery system 1200 that includes a gas bottle 1220 including $NO_2$ and an GENO cartridge 1210, which may be an implementation of GENO cartridge 1100 of FIG. 11, for converting $NO_2$ from the gas bottle 1220 to NO for delivery to a patient for NO inhalation therapy. The system 1200 is designed to be portable. In some implementations, the system 1200 may be designed to operate without the use of electronics or sensors. Depending on the capacity of the gas bottle 1220, the system 1200 generally has capability to deliver therapeutic NO gas for one to sixteen hours.

The system 1200 may be employed to deliver therapeutic NO gas to a patient on an emergency basis. Examples of such contexts include use by paramedics, military medics or field hospitals, and emergency rooms or a trauma center of a hospital.

Figure 13A:
Figure 13B:
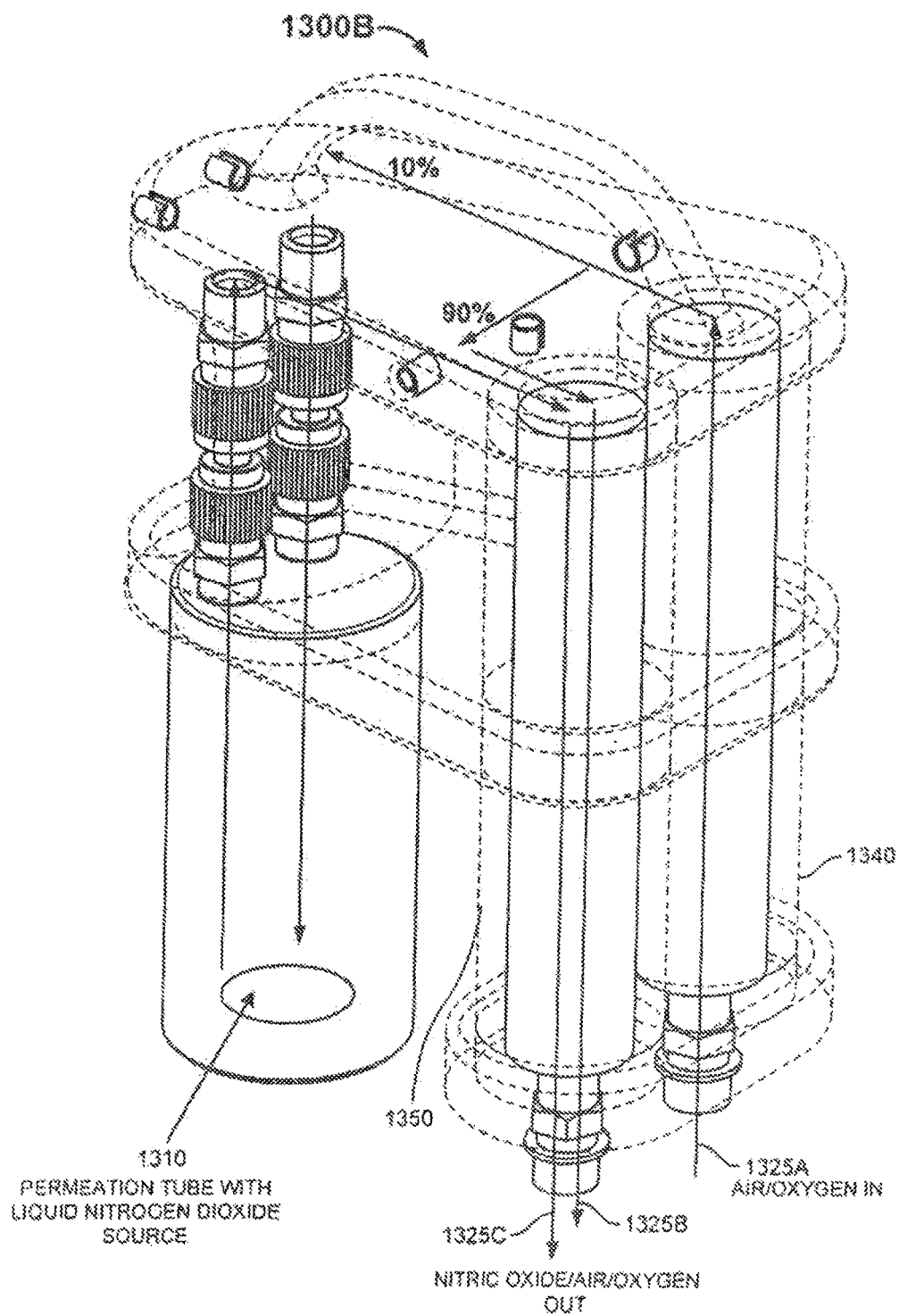

FIG. 13A depicts an exterior view 1300A of a therapeutic gas delivery system with a liquid $NO_2$ source. FIG. 13B illustrates an interior view 1300B of the therapeutic gas delivery system shown in FIG. 13A. The therapeutic gas delivery system includes a permeation tube 1310 with a liquid $NO_2$ source, which, for example, may be an implementation of the permeation device 935 of FIG. 9. The therapeutic gas delivery system also includes GENO cartridges 1340 and 1350. The GENO cartridge 1340 receives an air flow 1325a from an air or oxygen source. After exiting the GENO cartridge 1340, the air flow is divided such that approximately 10% of the air flow flows through the permeation tube 1310 by which gaseous $NO_2$ is diffused into the air flow. The air flow exiting the permeation tube 1310 and the other air flow that did not flow through the permeation tube 1310 flow through the GENO cartridge 1350, which converts the $NO_2$ to NO. The air flows 1325b and 1325c which exit the GENO cartridge 1350 are delivered to the patient for NO inhalation therapy. The permeation tube 1310 and the GENO cartridges 1340 and 1350 may be disposable.

Depending on the capacity of the permeation tube 1310, the therapeutic gas delivery system shown in FIGS. 13A and 13B may have the capability to deliver therapeutic NO gas for one to thirty days.

The therapeutic gas delivery system shown in FIGS. 13A and 13B is able to interface with a ventilator. The therapeutic gas delivery system shown in FIGS. 13A and 13B also may be employed to deliver therapeutic NO gas to a patient using a cannula. The use of the therapeutic gas delivery system with a cannula may enable NO therapy to occur outside of a hospital setting. One such example is the use of therapeutic gas delivery system for long-term NO therapy that takes place at the patient's home.

FIG. 13C depicts the exterior view 1300A of the therapeutic gas delivery system shown in FIGS. 13A and 13B relative to a soda can 1350. As illustrated, the implementation of the therapeutic gas delivery system shown in FIGS. 13A-13C is a small device relative to conventional NO inhalation therapy systems and is slightly larger than a soda can.

Figure 14:
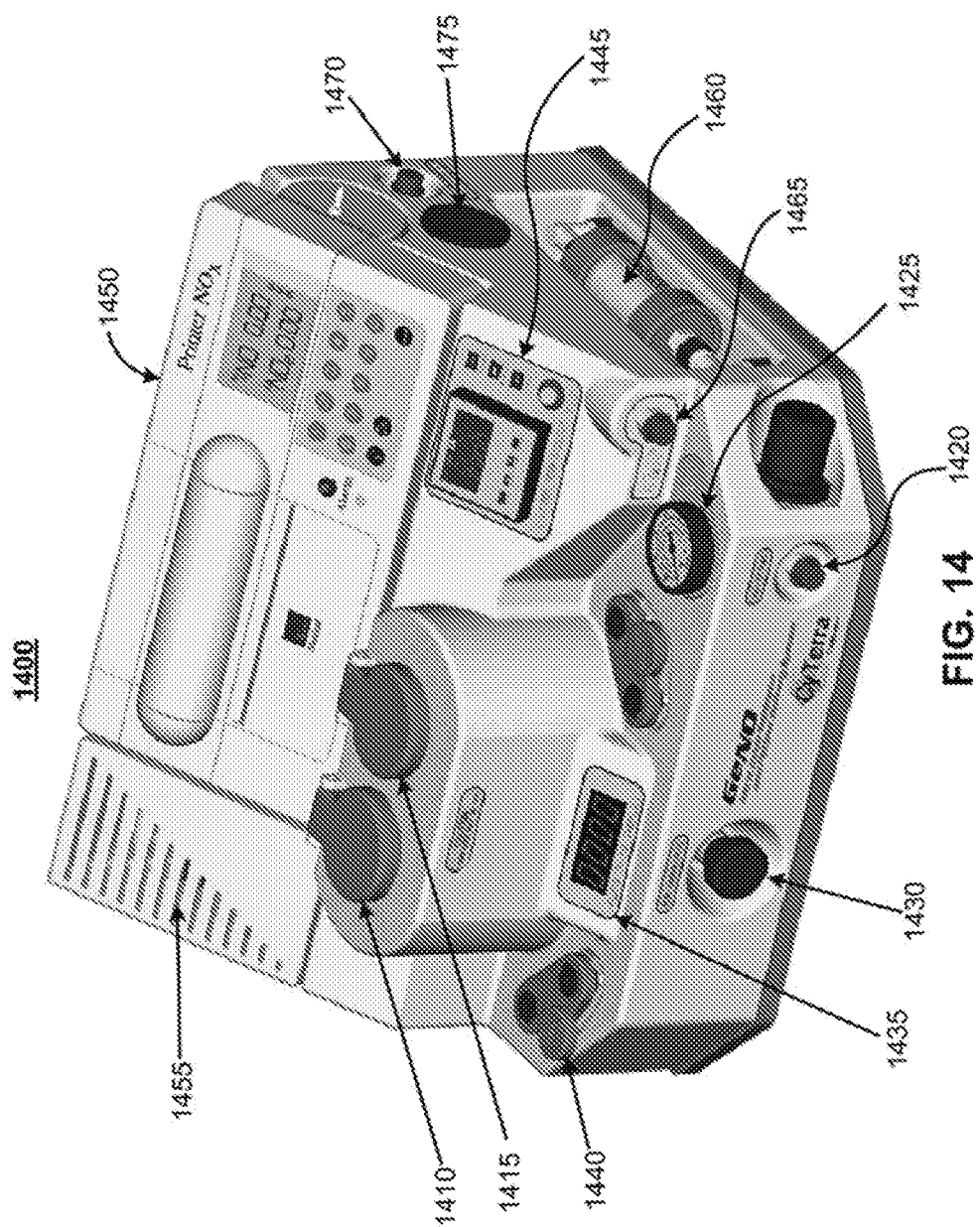

FIG. 14 depicts an exterior view of a therapeutic gas delivery system 1400 that uses GENO cartridges to convert $NO_2$ to NO for use in NO inhalation therapy. The system 1400 includes GENO cartridge ports 1410 and 1415 through which a GENO cartridge may be inserted or accessed. The system 1400 includes an inlet port 1420 through which air or oxygen flows into the system 1400 and an associated gauge 1425. The system 1400 includes a flow value 1430 and display 1435 for controlling the air flow. The system 1400 includes GENO cartridge flow ports 1440.

The system 1400 also includes a temperature controller 1445 and a NOx detector 1450, which is accessible through a NOx detector access 1455. The system 1400 also includes a GENO cartridge 1460 that is used to convert $NO_2$ to NO essentially just before the air flow having NO exits the system 1400 through the outlet 1465. The GENO cartridge 1460 may be referred to as a safety scrubber. The GENO cartridge 1460 may be smaller than the GENO cartridges used elsewhere in the system 1400. The system 1400 also includes a backup input port 1470 and an exhaust fan 1475.

Example 1

A cartridge six-inches in length with a diameter of 1.5-inches was used as the NO generation cartridge. Approximately 90 grams 35-70 sized mesh silica gel was soaked in a 25% ascorbic acid solution and air-dried at room temperature for two hours before being placed in the cartridge. A $NO_2$ permeation tube was used as the source gas for $NO_2$. Air from an air pump at a rate of 150 cc/min was flowed into the permeation tube and mixed, after it exited the cartridge, with 3 L/min of ambient air (which also was from the air pump). The permeation tube was placed in an oven with a temperature set at 32 degrees Celsius to provide a steady stream of 20 ppm $NO_2$ for the cartridge. The cartridge lasted for 269 hours before ceasing to convert 100% of $NO_2$ to NO, achieving breakthrough.

Example 2

Two cartridges were each filled using 35-70 sized mesh silica gel and approximately 40 grams of silica gel. The silica gel was prepared by being soaked with a 25% solution of ascorbic acid until complete saturation, and then dried in an oven for one hour at 240 degrees Fahrenheit. The ascorbic acid solution was prepared by mixing 25 grams of ascorbic acid in 100 ml of de-ionized water.

A 1000 ppm $NO_2$ tank was used to flow $NO_2$ through the two GENO cartridges at a rate of 150 cc/min. The two cartridges were placed in series. Ambient air from an air tank was mixed in after the $NO_2$ had passed through the first cartridge and been converted to NO. The air containing NO was then passed through the through the second cartridge in series. The air was passed through the cartridges at a rate of 3 L/min to create a total mixture of 40 ppm NO in air and free of any back reaction of $NO_2$.

The two cartridges converted 100% of the $NO_2$ for 104 hours. At the end of 104 hours, the experiment was stopped because the $NO_2$ tank was empty. The two cartridges had not yet reached breakthrough after 104 hours.

Results may be improved by drying the silica gel with a gas, such as nitrogen gas, to remove dripping water/ascorbic acid solution from the silica gel.

Example 3

A plastic PVC cartridge six-inches in length and having a diameter of 1.5-inches was used as the NO generator cartridge. The inside of the cartridge was filled with an ascorbic acid-silica mixture. To create the ascorbic acid silica mixture, approximately 108 grams of 35-70 sized mesh was used. The silica gel was soaked in 25% ascorbic acid solution and then baked in an oven for one hour at 240 degrees Fahrenheit. The ascorbic acid solution was prepared by dissolving 25 grams of ascorbic acid in 100 ml of de-ionized water.

A 1000 ppm $NO_2$ tank was attached to one end of the cartridge so that 1000 ppm of $NO_2$ flowed through the cartridge at a rate of 150 cc/min. The gas output of the cartridge was then mixed with air using an air pump that flowed at a rate of 3 L/min to create a total mixture of 40 ppm NO in air. This cartridge lasted for a total of 122 hours before achieving breakthrough.

A NOx detector detected a slight concentration of $NO_2$, varying from 0.15 ppm to 0.25 ppm. The concentration of $NO_2$ remained steady until breakthrough, making it likely that the detected $NO_2$ concentration was not a failure in the 100% efficiency of the cartridge but rather was $NO_2$ that was recreated in tubing after the cartridge. A second, smaller cartridge could be placed before the detector to eliminate the small $NO_2$ back reaction.

Example 4

A cartridge was prepared by using 35-70 sized mesh silica gel soaked in 25% ascorbic acid solution and air dried for approximately one hour. A permeation tube was the source for the $NO_2$ and a KinTek oven was used to raise the level of $NO_2$ required to 40 ppm. To achieve this concentration, the oven was set at 45 degrees Celsius. Air was delivered to the permeation tube using an air pump at the rate of 200 cc/min. Dilution air was also provided by the air pump at the rate of 3 L/min. To add humidity to the supply of $NO_2$, two jars filled with water were attached to the 200 cc/min air before the air entered the permeation tube. This helped to ensure that the air entering the $NO_2$ source would be moisture rich and therefore that the $NO_2$ entering the cartridge would also, be moisture rich. Approximately every five days, the water in the first jar receded, to below the end of the tubing and needed to be replenished so that the water level was above the bottom of the tube end. The second jar remained untouched for the entire length of the experiment. The cartridge lasted for 409 hours before ceasing to convert 100% of NO2 to NO, achieving breakthrough.

Example 5

A cartridge six-inches long and having a diameter of 1.5-inches was prepared by using 108 grams of 35-70 sized mesh silica gel. The silica gel was soaked in a 25% solution of ascorbic acid solution and dried at room temperature (approximately 70 degrees Fahrenheit) for approximately two hours. The air-dried silica gel was placed inside the cartridge.

A flow of 40 ppm $NO_2$ was sent through the silica-ascorbic acid cartridge at a rate of 3.2 L/min. The cartridge lasted for 299 hours before ceasing to convert 100% of $NO_2$ to NO, achieving breakthrough. The cartridge filled with air-dried silica gel lasted longer than a comparable cartridge filled with oven-dried silica gel. This demonstrates oxidation losses due to heating the ascorbic acid in the presence of air.

Example 6

Approximately 40 grams of 35-70 sized mesh silica gel was soaked in a 33% ascorbic acid solution and the dried in an oven at 240 degrees Fahrenheit before being placed in the cartridge. Ambient air at a flow rate of 3 L/min though an air pump was mixed with 1000 ppm of $NO_2$ from a tank at a flow rate of 200 cc/min, which created a total flow rate of 3.2 L/min and a total $NO_2$/air mixture of 60 ppm $NO_2$. The cartridge lasted for 25 hours before losing its 100% conversion ability. This demonstrates that using less silica gel/ascorbic acid in the cartridge results in a cartridge that does not last as long.

The use of NO generation cartridge in which $NO_2$ is quantitatively converted to NO is not limited to therapeutic gas delivery and may be applicable to many fields. For example, the NO generation cartridge may be included in an air pollution monitor. More particularly, the NO generation cartridge can also be used to replace high temperature catalytic converters that are widely used today in air pollution instrumentation measurement of the airborne concentration of $NO_2$ gas. The current catalytic converters expend significant electricity, and replacement of a catalytic convertor with a device that uses a NO generation cartridge may simplify the air pollution instruments, and enable lower cost, reduced weight, portable air pollution monitoring instruments.

Other implementations are within the scope of the following claims.

What is claimed is:

1. A method of delivering nitric oxide to a human comprising converting nitrogen dioxide to nitric oxide by fluidly communicating a gas flow including nitrogen dioxide to a receptacle including an inlet, an outlet, and a surface-active material comprising silica coated with an aqueous solution of an antioxidant, wherein the antioxidant includes ascorbic acid or a variant of vitamin E, wherein the inlet is configured to receive the gas flow and fluidly communicate the gas flow to the outlet through the surface-active material such that nitrogen dioxide in the gas flow is converted to nitric oxide.

2. The method of claim 1 wherein the surface-active material is saturated with the aqueous solution of the antioxidant.

3. The method of claim 1 wherein the surface-active material comprises a substrate that retains water.

4. The method of claim 1 wherein the variant of vitamin E includes alpha tocopherol or gamma tocopherol.

5. The method of claim 4 where the silica gel is 35 to 70 sized mesh.

6. The method of claim 1 wherein the receptacle comprises a cartridge.

7. The method of claim 1 wherein the antioxidant comprises ascorbic acid.

8. The method of claim 1 wherein the receptacle is at ambient temperature.

9. The method of claim 1 wherein the surface-active material is prepared using a solution of ascorbic acid in water.

10. The method of claim 9 wherein the surface-active material is prepared using a 20% solution of ascorbic acid in water.

11. The method of claim 9 wherein the surface-active material is prepared using a 25% solution of ascorbic acid in water.

12. The method of claim 9 wherein the surface-active material is prepared using a 30% solution of ascorbic acid in water.

13. The method of claim 1 wherein the surface-active material is prepared by soaking the surface-active material in a solution of ascorbic acid in water and air drying the surface-active material before inserting the surface-active material into the receptacle.

14. The method of claim 1 wherein the surface-active material is prepared by soaking the surface-active material in a solution of ascorbic acid in water and drying the surface-active material with a gas before inserting the surface-active material into the receptacle.

15. The method of claim 1 wherein the antioxidant comprises alpha tocopherol or gamma tocopherol.

16. The method of claim 1 wherein the receptacle includes screen and glass wool adjacent to both the inlet and the outlet.

17. The method of claim 1 wherein the screen and glass wool is soaked in the aqueous solution of antioxidant before being inserted in the receptacle.

\* \* \* \* \*